United States Patent [19]

Barak et al.

[11] 4,387,088
[45] Jun. 7, 1983

[54] NBD-ACIDIC PHALLOTOXINS AND THEIR USE IN THE FLUORESCENCE STAINING OF F-ACTIN

[75] Inventors: Lawrence S. Barak, West Bloomfield, Mich.; Eugene A. Nothnagel, Litchfield, Minn.; Watt W. Webb, Ithaca, N.Y.; Robert R. Yocum, Cambridge, Mass.

[73] Assignee: Cornell Research Foundation, Inc., Ithaca, N.Y.

[21] Appl. No.: 124,208

[22] Filed: Feb. 25, 1980

[51] Int. Cl.$^3$ .................. G01N 1/30; G01N 21/64; G01N 33/48; C07C 103/52
[52] U.S. Cl. .................................. 424/3; 260/112 R; 260/112.5 R; 424/7.1; 436/86; 436/800
[58] Field of Search .......................... 424/3, 7, 8, 177; 260/112.5, 112 R

[56] References Cited

PUBLICATIONS

Wieland, CRC Critical Reviews in Biochem., vol. 5, Issue 3, Dec. 1978, pp. 185–260.
Yocum, Lloydia, vol. 40, No. 2, Mar., Apr. 1977, pp. 178–189.
Barak, Proc. Natl. Acad. Sci. USA, vol. 77, No. 2, Feb. 1980, pp. 980–984.
Wulf, Proc. Natl. Acad. Sci. USA, vol. 76, 1979, pp. 4498–4501.

Primary Examiner—Anna P. Fagelson

Attorney, Agent, or Firm—Jones, Tullar & Cooper

[57] ABSTRACT

The present invention relates to novel compounds which are derivatives of acidic phallotoxins and correspond to the formula:

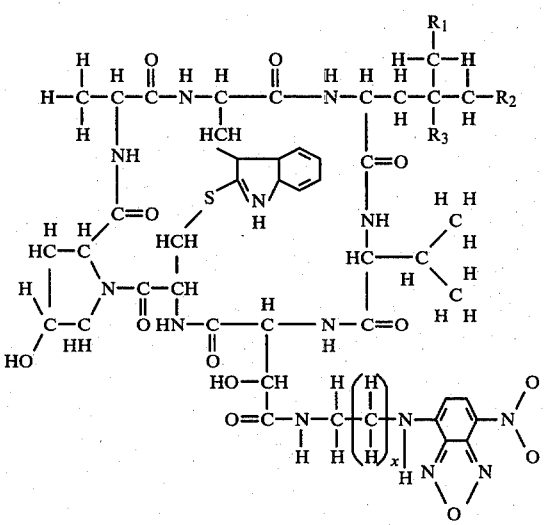

(NBD-acid phallotoxins) their preparation, and their use in fluorescent staining of F-actin.

15 Claims, No Drawings

NBD-ACIDIC PHALLOTOXINS AND THEIR USE IN THE FLUORESCENCE STAINING OF F-ACTIN

The United States Government has rights in this invention pursuant to Grant Nos. GM 21661-05 and CA 14454 and PCM 75-83068 awarded by the Department of Health, Education, and Welfare and the National Science Foundation, respectively.

The present invention relates to NBD-acidic phallotoxins, active fluorescent derivatives of the actin-binding mushroom toxins, such as Phallacidin, Phallisacin, Phallacin, etc., and to their synthesis. The present invention also relates to methods for staining F-actin, for example in cytoskeletal structures in living and fixed cultured animal cells and actively streaming algal cells. Actin binding specifically was demonstrated by competitive binding experiments and comparative staining of well known structures. Large populations of living animal cells in culture were readily stained using a relatively mild lysolecithin permeabilization procedure facilitated by the small molecular size of the label. F-actin in animal cells was stained in stress fibers, ruffles, the cellular geodome and in diffuse appearing distributions apparently associated with the plasma membrane. Staining of F-actin cables in algae with the NBD-acidic phallotoxins of the invention did not inhibit cytoplasmic streaming. NBD-acidic phallotoxins provide a convenient actin-specific fluorescent label for cellular cytoskeletal structures with promise for use in studies of actin dynamics in living systems.

Topographical fluorescence microscopy images of the major features of the cellular cytoskeleton have advanced the knowledge of cytoskeletal structures during the last few years. Labeling of fixed cells by indirect immunofluorescence with anti-actin antibodies or by fluorescent heavy meromyosin has been used to study microfilaments and their relationship with other cytoskeletal components. More recently, microinjection of fluorescent actin has been used to study these structures in living cells.

The present invention relates to a novel fluorescence staining composition which is used as a fluorescent marker for cellular F-actin and G-actin oligomers. It is applicable to living cells and thereby offers potential for observing the dynamics of cellular processes.

The acid phallotoxins derivatives of the present invention can be employed as fluorescent markers for actin which can be introduced conveniently into large populations of living cells, unlike fluorescent antibodies and myosin derivatives. Phallotoxins, small cyclic peptides have been shown previously to bind specifically and to stabilize F-actin, see T. Wieland and H. Faulstitch, *CRC Critical Reviews in Biochemistry*, 5, 184 (1978). In particular the acidic phallotoxin, phallacidin, that abounds in American strains of the poisonous mushroom *Amanita phalloides* offers small molecular size (molecular weight of 847) and a convenient carboxylic acid residue for attachment of the fluorescent label as described by R. R. Yocum and D. M. Simons in *Lloydia*, 40 (2), 178–179 (1977). Although this toxin differs in this carboxylic acid residue from phalloidin, its actin binding characteristics are essentially identical.

SYNTHESIS OF AN NBD DERIVATIVE OF PHALLACIDIN

Phallacidin was purified by column chromatography from a mixture of mushroom toxins residual to an amanitin purification. This purification is well known to one skilled in the art as exemplified in a procedure by R. R. Yocum in *Biochemistry*, 17 (18), 3786–9 (1978). Phallacidin is represented by structural formula I.

FORMULA I

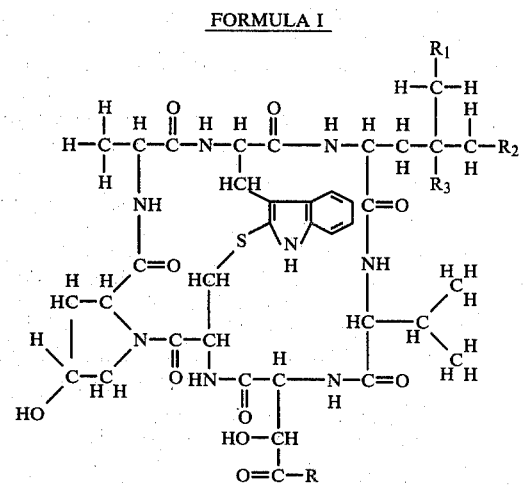

wherein R is —OH, and $R_2$ is H and $R_1$ and $R_3$ are —OH.

The phallacidin was obtained as a byproduct of an amanitin purification. After the first neutral LH-20 Sephadex (Pharmacia) chromatography, the phallacidin fraction was still contaminated with a dark brown polar material. Three additional steps, A, B and C removed most contaminants providing purified phallacidin toxin.

In step A, crude phallacidin plus phallisacin from 100 gm of *A. Phalloides* were chromatographed on a 25 mm×200 cm LH-20 column in 0.1 N acetic acid. Phallacidin eluted between fractions 125–150. 1.5 ml of this crude fraction containing approximately 60 mg of toxin was placed on a 1.5 cm×400 mm LH-20 column and eluted with 0.08 N acetic acid at 7 ml/hr. The majority of brown material eluted in the early fractions, whereas the phallacidin eluted between 78 and 110 ml. The pooled phallacidin fractions were neutralized with ammonium hydroxide to pH 7.0, reduced to a volume of 1 ml on a rotovaporizer, desalted on a Sephadex G-25 column and chromatographed a second time on LH-20.

In step B, the toxin fraction obtained from step A was applied to QAE Sephadex prepared as described by Yocum in a 1.1 cm×15 cm column. A stepwise salt gradient of 0.05 N NaCl intervals was used to develop the column. The phallacidin eluted between 0.05 and 0.3 N NaCl leaving brown material remaining on the column. The toxin was again concentrated and desalted as in step A above.

SP-50 Sephadex was equilibrated with 0.5 N ammonium acetate at pH 6.5 and then washed with 5 volumes of water in a Buchner funnel. The Sephadex was then placed in a column and washed with two more volumes of water. The concentrated material from B was placed on a 1.5 cm×5 cm cation exchange column of SP-50 Sephadex. The column was first eluted with water. Phallacidin, which eluted in the flow through, was then applied to Amberlite XAD-4 (Rohm & Haas) in a 2 cm×5 cm Buchner funnel fitted with a 25–50 μm fritted-glass disk. The amberlite has been cleaned with sequential 8–12 hour washes in 1 N NaOH, 1 N HCl, chloroform, 95% ethanol, and water. The amberlite was washed with 40 ml of distilled water and then the toxin was eluted with 40 ml of absolute ethanol. The toxin solution had a slight brown color after being concentrated to 1 ml. However, no impurities were detectable as alterations in the phallacidin 240320 nm absorption spectrum.

The following steps produce the desired phallicidin derivative from the purified phallicidin obtained in step C.

In step D, the toxin solution from step C was dried in a rotovaporizer and redissolved in dimethylformamide (DMF) at a concentration of 56 mg/ml. The solution was placed over dry ice and an excess of diazomethane in ether was added at 76° C. in a well ventilated hood. The mixture was allowed to warm up to room temperature for 5-10 minutes after which the DMF and diazomethane were removed under high vacuum in a rotovaporizer. This converted the phallacidin carboxylic acid residue to a methyl ester as represented in Formula I wherein R is—$OCH_3$.

The dried material was redissolved in water and a fraction was removed for thin layer chromatography (TLC). TLC showed that 50-60% of the toxin had been altered. The toxin solution was redried, dissolved in ethylene-diamine and left at room temperature for 90 minutes. The excess ethylenediamine was removed under reduced pressure and the dried material was placed in 1 ml of water at 4° C. for 1.5 hours.

The toxin solution was placed on an SP-50 Sephadex column equilibration with 0.5 N ammonium acetate at pH 6.5. The material at this time contained a yellow-green impurity. Upon application of the toxin solution to the SP-50 column, a colored fraction eluted in the flow-through whereas another remained bound to the column and eluted between 0.1-0.5 N NaCl. This second fraction contained the ethylenediamine-linked material as represented by Formula I wherein R is —NH—$CH_2$—$CH_2$—$NH_2$. The yield of the reaction as shown by UV absorption at 292 nm was 54% using $\epsilon_{292} = 1.1 \times 10^4$/1-M-cm.

The ethylenediamine phallacidin (N-Ph) fraction was desalted on Amberlite, concentrated, and placed on a 1.1 cm×24 cm LH-20 Sephadex column equilibrated with 0.02 N acetic acid. The column was developed at 3.5 ml/hr. Greenish toxin containing material eluted earlier than the pure ethylenediamine-linked derivative found between 14 and 27 ml. The purified toxin fractions were pooled, desalted on Amberlite, redissolved in water and lyophilized. There were stored dessicated at 4° C. until later use. The final purification yielded 7.7 mg off pure material as shown by UV absorption.

In step E, approximately 200 μg of the purified material of step D was dissolved in 200 μl of absolute methanol plus 4 μl of anhydrous pyridine. 50 μl of freshly prepared 10 mg/ml 4-chloro-7-nitrobenz-5-oxa-1,3-diazole, (NBD-Cl) (Molecular Probes) in methanol was added. The materials reacted for 12 minutes at 70° C. over an oil bath. The solution was reduced to 50 μl with dry nitrogen and allowed to react for 5 minutes more at 50° C. 600 μl of diethylether was added to the solution and a brownish precipitate formed. The solution was centrifuged and the supernatant removed. The toxin containing precipitate was resuspended in 20-30 μl of absolute methanol and the procedure repeated three more times with 400-600 μl of diethylether per extraction to remove free NBD-Cl.

In step F, Sp-50 Sephadex was prepared as in step C. The NBD-ethylenediamine phallacidin (hereinafter NBD-phallacidin or NBD-Ph) was dissolved in 200 μl of water and placed on the column. Yellow colored material, the NBD-Ph, eluted in the flow-through whereas unreacted toxin and brownish material, probably a salt of pyridine and NBD-Cl, eluted in the NaCl fractions. The NBD-phallacidin (NBD-Ph) is represented by structural Formula II:

FORMULA II

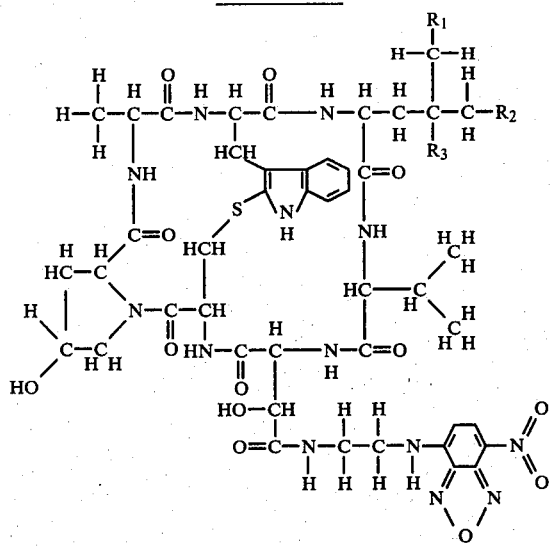

wherein $R_2$ is H, and $R_1$ and $R_3$ are —OH.

Step G represents equilibrium dialysis experiments which were performed in order to determine whether the N-Ph bound to actin. Buffer A consisting of 5 MM Tris HCl (pH 7.4) and 0.1 mM ATP and buffer B consisting of buffer A plus 2 mM $MgCl_2$ were prepared immediately before use. 3.05 mg actin (Sigma) and an equal amount of 5× crystalized ovalbumin (Calbiochem) were dissolved in separate volumes of 2 ml of buffer A. The fractions were split into four 1 ml aliquots. 21 μg of N-Ph in 1 ml of buffer was added to each of the four opposing compartments in the dialysis chambers. Dialysis was performed overnight at 4° C.

In step H, in order to asess whether the amino-linked phallacidin enhanced actin polymerization, the viscosity of solutions containing N-Ph was measured. Viscosity measurements were performed in an Ostwald Dropping Pipette with a 2 ml volume. The viscometer was cleaned before each measurement. The dialyzed actin and toxin containing chambers as in step G were diluted to ⅓ their concentration with buffer B. Relative viscosities were determined from the average of 3-5 measurements.

TABLE II

| Viscosity Measurements of Actin Solutions | |
| --- | --- |
| Solution | Relative Viscosity |
| 1. Water | 1 |
| 2. '1' + Tris | 1 |
| 3. '2' + Toxin | 1 |
| 4. Actin + '2' | 1.11 |
| 5. '4' + Toxin | 1.25 |

In step I, Thin Layer Chromatography (TLC) was performed on the various phallacidin derivatives. All samples were run on Silica Gel-60 F254 plates (E. Merck) in sec-butanol/ethyl acetate/acetic acid/water (140/120/2/50). In Table I are the TLC results of the various phallacidin derivatives. Because the ethylendiamine phallacidin has a free amino group, it is immobile on silica gel in the solvent systems used. The disappearance of the mobile spot containing phallacidin methyl ester indirectly indicated the reaction with ethylenediamine was successful. The major fluorescent spot of the NBD-Cl phallacidin reaction was eluted from silica gel and the 240-320 nm absorption spectrum was measured. It showed both toxin and fluorophore in the same spot. The absorption spectrum of N-Ph, see step D, was from 240-320 nm. The peak at 290 is characteristic of the thioether tryptophan linkage and indicates that this portion, necessary for toxin activity, is still intact. This spectrum is equivalent to that of phalloidin.

TABLE I
THIN LAYER CHROMATOGRAPHY

| Compound | R Values |
| --- | --- |
| Phalloidin | .32 |
| Phallacidin | .16 |
| Phallacidin Methyl Ester | .37 |
| Ethylenediamine Phallacidin | <.05 |
| NBD-Phallacidin | .42 |

Phallotoxins stabilize and bind to F-actin. Therefore dialysis and viscosity experiments were performed to test whether the amino altered phallacidin derivative still retained this property. If so, it could be expected to show binding to actin upon dialysis and promote an increase in viscosity of actin solutions. The dialysis measurements did show N-Ph binding to actin with respect to ovalbumin. The viscosity measurements presented in Table II indicated that N-Ph increased the state of actin polymerization. The toxin was subsequently labeled with NBD and was tested to determine if this labeled derivative retained biological activity. The impure NBD-Ph toxin fraction successfully stained actin cables in both fixed and living tissue culture cells and in perfused cells of the algae *Chara australis*. It would be competitively inhibited from actin binding by an excess of unlabeled phalloidin.

The absorption and emission spectrum of the purified fluorescent purified NBD-ethanolamine has extinction coefficients $\epsilon 470 = 2.4 \times 10^4$/1-M-cm and $\epsilon 346 = 9 \times 10^3$/1-M-cm. Assuming that the fluorophore extinction coefficients remain the same after coupling to the toxin and are known exactly, a ratio of 1.27 mol toxin/mol NBD was calculated. In other words, at least 79% of the toxin from step F is labeled. The cumulative reaction yield was 13% to N-Ph. Typical yields of NBD reaction varied between 20-25%.

In the same manner as phallacidin, any compound corresponding to the formula:

FORMULA I

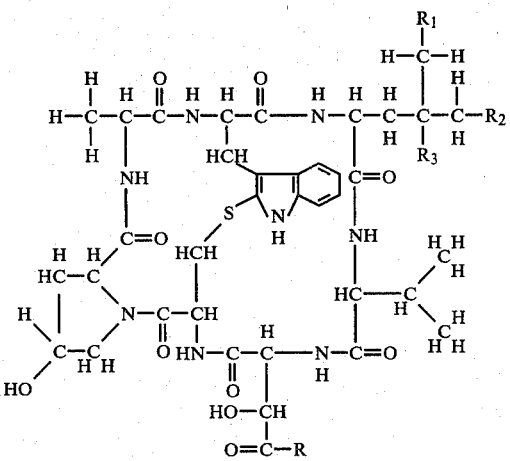

wherein R is —OH, and $R_1$, $R_2$, and $R_3$ are independently selected from the group consisting of —H and —OH, can be reacted to form a compound corresponding to the formula:

FORMULA IV

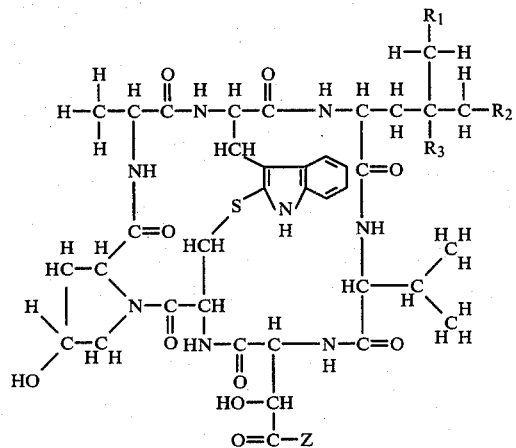

where $R_1$, $R_2$ and $R_3$ are independently selected from the group consisting of —H and —OH, where Z is

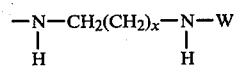

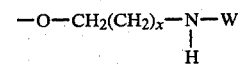

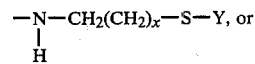

where x is 0 or a whole number, preferably 1-10, most preferably 2-10, where W or Y are organic fluorophores such as

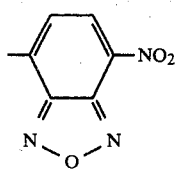

or the moiety resulting from reacting a terminal amino group or sulphydryl group with compounds such as fluorescein-5-maleimide or the like. Other examples of W include the reaction products of the terminal amino group with compounds such as lissamine, rhodamine B sulfonyl chloride, dansyl chloride, fluorescamine, fluorescein-isothiocyanate, 5 or 6 (3,5-dichlorotriazinyl)amino fluorescein (5 or 6 DCTAF), and like compounds where the fluorescein associated with the reading group is replaced by moieties derived from rhodamine B, tetramethyl rhodamine, eosin and the like.

The amino group can be inserted into the acid phallatoxin molecule by, for example, reacting the carboxyl group in a manner to insert the amino group e.g.

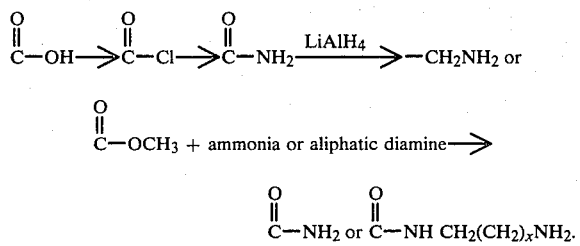

The terminal amino group can be converted to the mercapto group or the mercapto group can be inserted in the molecular by reacting the acid group or its methyl ester with lysine or a similar difunctional compound. The individual reaction steps required to form the compounds of the formula IV are all within the skill of the art. The resultant compounds of Formula IV are useful in the same manner as the NBD-phallacidin specifically exemplified herein, and are useful to study F-actin and G-actin oligomers in vivo and in vitro.

METHOD OF STAINING LIVING CELLS

Living cells were permeabilized by standard techniques as in the method of M. R. Miller et al. as described in Experimental Cell Research, 820, 421–425 (1979) using a solution of 14–40 μg/ml of palmitoyl lysophosphatidyl choline (Sigma) in a high glucose buffer, buffer A, consisting of: 120 mM $NaCl_2$, 15 nM glucose, 10 nM Hepes, 4.4 mM $NaHCO_3$, mN KCl, and 1 mM $Na_2PO_4$ adjusted to pH 1,7 with 1 N NaOH. Two stain exposure methods were developed. In method I the cells were washed four times with buffer A to remove the lysolecithin after two minutes and then stained for five minutes with 5 ng of the purified NBD-phallacidin in 350 μl of buffer A at room temperature. The cells were then washed three times and viewed within 1 hour. In method II cells were washed one time and then stained for five minutes with NBD-phallacidin dissolved in DMEM plus 10% FCS in the 37° C. These cells were then transferred to warm medium and held in the incubator.

For tests of viability flurescin diacetate (Sigma) in stock solution at 2 mg/ml acetone was applied at 0.5 μl per ml of cell medium and cells were inspected promptly for reactive staining.

LABELING OF ACTIN CABLES IN ACTIVELY STREAMING CHARA AUSTRALIS

Internodal cells of Chara australis were isolated from the plant and were placed in petri dishes containing artificial pond water. To facilitate microscopic viewing, "windows" through the dense chloroplast layer were produced by the technique of E. Kamitsubo as described in Experimental Cell Research, 74, 613–616 (1972). Within 10 days the actin cables returned to the window area, and at that point the cells were perfused following the technique of M. Tazawa et al. as described in Cell Structure Function, 1, 165–176 (1976), (13) with 1.5 μg of NBD -Ph dissolved in 50 μl of Tazawa's perfusion fluid consisting of 30 mM hepes, 5 mM EGTA, 6 mM $MgCl_2$, 1 mM ATP, 23.5 mM methanesulfonic acid, and 250 mM sorbitol (pH-7 as adjusted with KOH). Photographs were recorded approximately one hour after perfusion.

Fluorescence photomicrographs were taken using epifluorescent illumination from either a mercury lamp or the 448 nm line of an argon laser. The last-illuminated photomicrographs often appear somewhat mottled due to optical interference.

Fixed fibroblastic cells of various common forms stained with NBD-phallacidin display the general features of the actin cytoskeleton which were expected from recent indirect immunofluorescence experiments with actin antibody. To illustrate, with fixed and stained chick embryo fibroblasts in NBD-phallacidin fluorescence, the expected actin stress fibers and fiber bundles are clearly marked. There is no nuclear staining.

Competitive staining experiments on CEF designed to test specificity were conducted under 1500 magnification. The cells in one group were stained by the standard procedure with NBD-phallacidin analog and in a second group with an accompanying 50 fold excess of unlabeled phalloidin. 3T3 cells (not shown) give similar results. The CEF cells demonstrate diffuse membrane staining, and an abundance of stained cables. The paired dish, stained in the presence of competing phalloidin showed only very weak levels of possibly non-specific staining. The specificity of the fluorescent labeled toxin was thus established.

For comparison, 3T3 cells labeled with free NBD-Cl show prominent nuclear and very little peripheral fluorescent. NBD-ethanolamine produces low levels of diffuse fluorescence. The features of these stains are clearly distinguishable from the toxin staining.

Living fibroglastic cells permeabilized with lysolecithin and stained with NBD-phallacidin have fluorescence and phase contrast images that are virtually indistinguishable from similar cells that have been fixed and stained. However, detailed microscopic examination (1500 magnification) of the fluorescence of these cells does show that it depends sharply on depth and plane of focus, indicating the three dimensional features of the actin cytoskeleton, whereas the fixed cells used in the present invention tend to collapse somewhat. There is also a tendency for some micro-filament bundles to display a more feathery and slightly curvilinear appearance than is usually observed in fixed cells.

Prominent actin structures in the ruffles at the perimeter of an active lamellipodium were examined. Most of the actin filament bundles extending into the lamellipodium from the cell center appear to terminate well before reaching the periphery.

An MEF cell, or cells, was photographed in mitosis. Here the cleavage furrow associated actin separating the two cell volumes was clearly visible. No fibrous organization of the actin was visible in any plane of the fluorescence images. Three NBD-phallacidin fluorescence images of MEF's (1250 magnification) illustrated the diversity of virtually unaltered cytoskeletal structures that can be captured. In one the actin "Cellular geodome" sometimes seen in rounded cells was preserved. In another a round cell that has just begun to spread shows prominent actin structures in its regularly ruffled border and evidence of early axial alignment of central actin cables. One could imagine that the cytoskeletal structure shown in the third represented a later stage of development. A prominent cross banded actin network terminates the central region of quasi-radial actin bundles.

Effects on living fibroblasts of the permeabilization treatment and toxin staining were appraised for structural perturbations and reduction of cell viability over both short and long times by microscopic observations and by fluorescein diacetate (FDA) reactive staining. This well established staining method provided a convenient objective measure of the recovery of membrane integrity and cell viability and is demonstrated by B. Rotman and B. W. Papermaster in *Proc. Nat. Acad. Sci. USA*, 55, 134–141 (1966).

M. R. Miller et al., supra, had established by assays of DNA synthesis and membrane leakage that their lysolecithin permeabilization procedure (without toxin staining) left cells viable for at least sixty minutes after permeabilization. In the present invention it was found that in surveying a wide range of conditions that short term recovery, as defined by FDA staining and cell appearance, was quite sensitive to details of the permeabilization procedure and subsequent conditions during recovery. The viability was retainable at toxin levels necessary to provide adequate actin staining. FDA staining after sixty minutes was retained even with an indrease of the NBD-phallacidin dose to 2-3 $\mu$g/ml; where the cells were incubated with NBD-phallacidin in medium with serum.

In summary, the effects on living fibroblasts of the lysolecithin permeabilization process and accompanying toxin staining of the present invention include the following: (1) The doses required for adequate staining of virtually all cells in a dish introduces no initial visible perturbation of the cell structure. (2) Viability of toxin stained cells as assayed after 60 minutes by FDA fluorescence generally approximately or exceeded 33% but is variable and sensitive to the lysolecithin permeabilization treatment. (3) Several fold increases of the dose of lysolecithin above the standard levels induces rapid cell loss. (4) In a few cases the MEF's concentrate the fluorescent marker into internal spherical structures that may be vesicles. Similar structures have recently been observed subsequent to fluorescent actin microinjection by T. E. Kreis et al in *Proc. Nat. Acad. Sci. USA*, 76, 3814–3818 (1979). Although long term studies are incomplete and variable in their results, the observations from the present invention together with those of M. R. Miller et al., supra, suggest that some of the permeabilization and staining procedures leave cells viable by the FDA assay for many hours.

The following discussion deals with working actin cables in living *Chara* during cytoplasmic streaming.

The giant cells of *Characean algae* show rapid rotational cytoplasmic streaming. Electron and fluorescence microscopic studies employing myosin fragments having identified subcortical actin cables which are believed to participate in the generation of the streaming in these cells. These cables form unambiguous structures attached to the chloroplast files. Living, streaming Chara cells perfused with NBD-phallacidin show fluroescent subcortical actin cables whereas control cells perfused with NBD-Cl and NBD-ethanolamine show no fluorescent cables. Structural features of the actin cable network marked by NBD in these living cells confirm features previously observed in fixed cells marked with myosin fragments such as reported by R. E. Williamsom in *Nature*, 248, 80102 (1974).

The fluorescent stain on some cables appears somewhat fuzzy. Electron microscopy has previously revealed endoplasmic filaments in association with actin cables. Unresolved fluorescence in one instance may consist of aggregates of these submicroscopic filaments which have bound NBD-phallicidin, but artifacts have not been excluded.

It is to be emphasized that the photomicrographs made showed cells which were actively streaming at near normal rates. Labeling with myosin fragments stops streaming. The fluorescent marked cables during the continuation of cytoplasmic streaming were observed in the present invention for several hours following NBD-phallacidin perfusion. This capability for observing the actin cytoskeleton in living cells has made possible the studies of the dynamics of cytoplasmic streaming in future studies.

In conclusion, the present invention has shown in both tissue culture cells and algal cells that NBD-phallacidin labels a variety of structures known to consist of F-actin. Moreover, phalloidin competition experiments and control stainings show that the staining is specific for F-actin.

The present invention has observed with NBD-phalladicin large amounts of diffuse and fibrous actin that appear to be membrane associated. Because the diffuse staining is similar in living cells that are permeabilized and stained, and in fixed and stained cells, it seems unlikely to be due to an artifact. Of course, phallacidin does stabilize F-actin and may therefore induce association of dissolved G-actin or F-actin fragments with membrane-associated F-actin. Similarly, cross-linking by the fixative in fixed and stained cells may accomplish a similar aggregation.

The cell nuclei are not stained by NBD-Phallacidin in either live or fixed tissue culture cells. In contrast, photographs of actin antibody staining show staining of cell nuclei as shown by W. W. Franke et al., in *J. Cell Biol.*, 81, 570–580 (1974). This difference implies that either the nuclear actin is entirely monomeric G-actin which does not bind the toxin or that the actin antibodies have stained nuclei non-specifically.

Through the use of NBD-phallacidin florescent stain all of the structures in live cells can be observed with as excellent resolution as those in fixed cells such as stree fibers, ruffled borders, and diffuse membrane actin. Since the cells are not fixed, there is no distortion introduced by the fixation procedure. One might worry that the lysolecithin treatment may alter cytoskeletal structure, but after the staining treatment of the present invention no gross morphological alterations in structure of various known cell forms was observed in cells in which the actin distribution was observed. Because the toxin enters the cells uniformly by diffusion through the permeabilized membrane, its concentration and rate of delivery are smoothly regulated. It is believed that in this way cellular damage and artifact formation are minimized in comparison with microinjection. Perhaps it is this difference of treatment that has prevented formation of the localized aggregates of actin seen by Wehland et al. in *Proc. Nat. Acad. Sic. USA*, 74, 5613-7 (1977), upon microinjecting phalloidin into live cells followed by fixing and indirect actin staining.

Both phallacidin and lysolecithin permeabilization do perturb living fibroblasts but effects on structure have been unobservable by light microscopy and viability loss appears relatively slow. The effects of NBD-phallacidin on the dynamics of cytoskeletal change, the effects on viability or the optimization of the staining procedures to minimize perturbation of cellular processes have not fully been characterized. Nevertheless the fluorescent toxin of the present invention should prove useful as a probe to observe some aspects of cytoskeletal change in animal cells.

Observations of actin filament configurations and movements during cytoplasmic streaming in the living, perfused algal cells of *Chara australis* were made possible by use of NBD-phallacidin. This experiment illustrates the usefulness of the toxin as an In vivo actin marker that enables observation of previously inaccessible dynamic processes. Such observations must be interpreted carefully because phalloidin and phallacidin are known to stabilize F-actin and hence may alter the native degree of actin polymerization in live cells. In the Chara experiments the toxin is not disruptive and this observation suggests that depolymerization of actin is not an essential step in the pumping of cytoplasmic streaming in these cells.

Fluorescence labeled phallacidin is a preferred actin stain, because phallacidin is extremely stable and is relatively abundant in *Amanita phalloides* its availability is assured. The low molecular weight of the labeled toxin allows its introduction into slightly permeabilized living tissue cells. Because permeabilization procedures are applicable *en masse* to an entire culture dish population, the overall procedure provides a large sampling of a cell population in contrast with microinjection techniques.

We claim:

1. A compound corresponding to the formula:

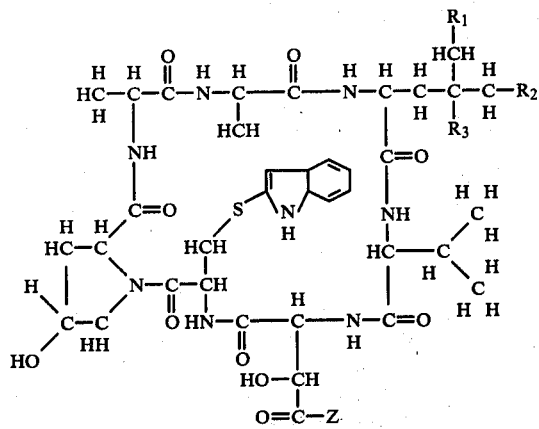

wherein $R_1$, $R_2$, and $R_3$ are independently selected from the group consisting of H and OH and Z is an organic moiety which is a fluorophore derived from fluorescein, rhodamine B, tetramethyl rhodamine or eosin.

2. The compound of claim 20 wherein $R_1$ and $R_3$ are OH and $R_2$ is H.

3. A compound corresponding to the formula of claim 1 where Z is

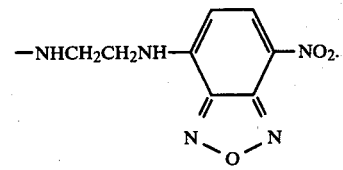

4. A process for the preparation of a compound as in claim 1 which comprises:

(a) reacting a compound corresponding to the formula:

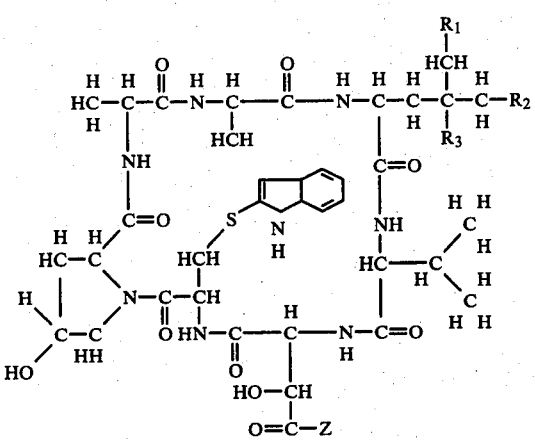

wherein $R_1$, $R_2$, and $R_3$ are indepedently selected from the group consisting of H and OH, with (B) diazomethane to form the methyl ester of the carobxyl group (C) reacting the resultant methyl ester with ethylenediamine to form an

in place of the methyl ester

and (D) reacting the resultant

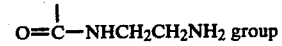

with 4-chloro-7-nitrobenz-2-oxa-1,3-diazole to form the

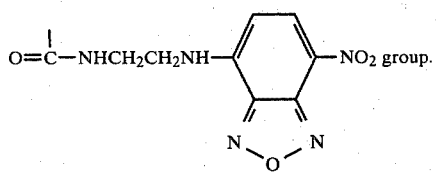

5. The process of claim 4 wherein $R_1$ and $R_3$ are —OH and $R_2$ is —H.

6. A process for the preparation of a compound as in claim 1, which comprises reaction of the carbonyl group

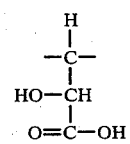

to form a terminal amino or sulphydryl group and reacting the resultant amino or sulphydryl group with a member of the group consisting of 4-chloro-7-nitrobenz-2-oxa-1,3-diazole, fluorescein-6-maleimide, lissamine rhodamine B sulfonyl chloride, dansyl chloride, fluorescamine, fluoresceinisothiocyanate, or 5 or 6 (3,5-dichlorotriazinyl)amino fluorescein.

7. A method of fluorescent staining F-actin and G-actin oligomers which comprises contacting said actin with a fluorescent stain comprising a compound as in claim 1 to bind said compound to said actin, thereby staining said actin.

8. A method as in claim 7 wherein the actin is stained within a living cell.

9. A method as in claim 7 wherein the actin is stained within a fixed cell.

10. A method of fluorescent staining F-actin and G-actin oligomers which comprises contracting said actin with fluorescent stain comprising the compound of claim 3 to bind said compound to said actin, thereby staining said actin.

11. A compound corresponding to the formula:

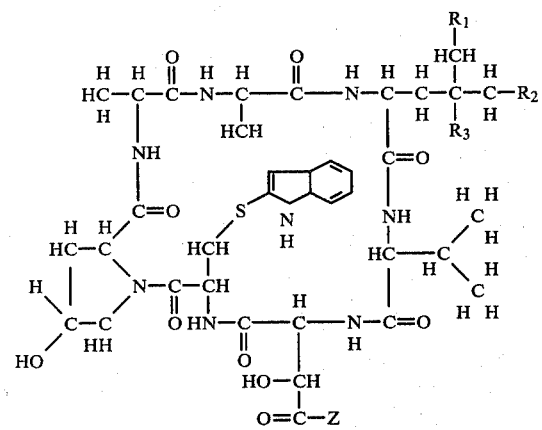

wherein $R_1$, $R_2$, and $R_3$ are independently selected from the group consisting of H and OH and Z is a fluorophore derived from fluorescein-5-maleimide, lissamine rhodamine B sulfonyl chloride, dansyl chloride, fluorescamine, fluoresceinisothiocyanate, 5 or 6 (3,5-dichlorotriazinyl)amino fluorescein, or

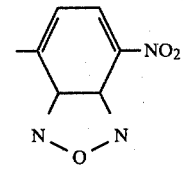

12. A compound corresponding to the formula:

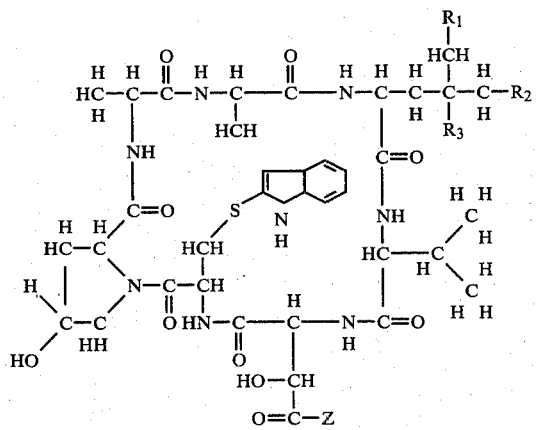

wherein $R_1$, $R_2$, and $R_3$ are independently selected from the group consisting of H and OH and Z is selected from the group consisting of:

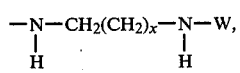

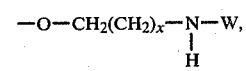

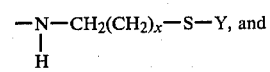

where x is a whole number and W and Y are

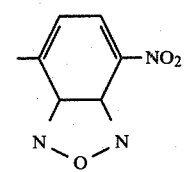

or the moiety resulting from the reaction of a terminal amino group or sulphydryl group with fluorescein-5-maleimide, lissamine rhodamine B sulfonyl chloride, dansyl chloride, fluorescamine, fluoresceinisothiocyanate, or 5 or 6 (3,5-dichlorotriazinyl)amino fluorescein.

13. The compound as in claim 12 wherein x is 1–10.
14. The compound as in claim 13 wherein x is 2–10.
15. The compound as in claims 12, 13 or 13 wherein W and Y are

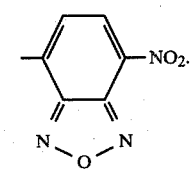

* * * * *

UNITED STATES PATENT AND TRADEMARK OFFICE
CERTIFICATE OF CORRECTION

PATENT NO. : 4,387,088
DATED : June 7, 1983
INVENTOR(S) : Lawrence S. Barak et al.

It is certified that error appears in the above-identified patent and that said Letters Patent is hereby corrected as shown below:

Column 12, claim 2, line 3, "claim 20" ahould read
-- claim 1 --.

Column 12, claim 4, line 46, "carobxyl" should read
-- carboxyl --.

Column 13, claim 10, line 40, "contracting" should read
-- contacting --.

Signed and Sealed this

Thirtieth Day of August 1983

[SEAL]

Attest:

GERALD J. MOSSINGHOFF

Attesting Officer

Commissioner of Patents and Trademarks